United States Patent [19]

Massett et al.

[11] Patent Number: 4,467,090

[45] Date of Patent: Aug. 21, 1984

[54] COMPOUND, 8-FLUORO-5-(P-FLUOROPHENYL)-2-[4-(P-FLUOROPHENYL)-4-HYDROXYBUTYRYL]-2,3,4,5-TETRAHYDRO-1H-PYRIDO[4,3-B]INDOLE

[75] Inventors: Stephen S. Massett; Harry A. Watson, Jr., both of Groton, Conn.

[73] Assignee: Pfizer Inc., New York, N.Y.

[21] Appl. No.: 425,152

[22] Filed: Sep. 30, 1982

[51] Int. Cl.$^3$ ............................................. C07D 471/04
[52] U.S. Cl. .......................................... 546/85; 546/86
[58] Field of Search ............................................ 546/85

[56] References Cited

U.S. PATENT DOCUMENTS 4,001,263  4/1977  Plattner et al. ...................... 546/85
4,224,329  9/1980  Welch .................................. 424/256

OTHER PUBLICATIONS

Fieser & Fieser, Reagents for Organic Synthesis, vol. 3, pp. 260–261, Wiley-Interscience.
Harbert et al., J. Med. Chem. 23, pp. 635–643 (1980).

Primary Examiner—Alan L. Rotman
Attorney, Agent, or Firm—Charles J. Knuth; Albert E. Frost; Robert K. Blackwood

[57] ABSTRACT

8-Fluoro-5-(p-fluorophenyl)-2-[4-(p-fluorophenyl)-4-hydroxybutyryl]-2,3,4,5-tetrahydro-1H-pyrido[4,3-b]-indole; processes therefor; and process for the conversion to flutroline.

1 Claim, No Drawings

COMPOUND, 8-FLUORO-5-(P-FLUOROPHENYL)-2-[4-(P-FLUOROPHENYL)-4-HYDROXYBUTYRYL]-2,3,4,5-TETRAHYDRO-1H-PYRIDO[4,3-B]INDOLE

BACKGROUND OF THE INVENTION

This invention relates to processes for the preparation of 8-fluoro-5-(p-fluorophenyl)-2-[4-(p-fluorophenyl)-4-hydroxybutyl]-2,3,4,5-tetrahydro-1H-pyrido[4,3-b]indole (flutroline), a neuroleptic agent having valuable therapeutic activity, see Plattner et al., U.S. Pat. No. 4,001,263, and Herbert et al., J. Med. Chem. 23, pages 635–643.

Plattner et al. and Harbert et al. also describe the earliest synthesis of flutroline: p-fluorophenylhydrazine is condensed with N-carbethoxy-4-piperidone to form 8-fluoro-2-carbethoxy-2,3,4,5-tetrahydro-1H-pyrido[4,3-b]indole. By the Ullman reaction the latter is arylated to form the 5-(p-fluorophenyl) derivative and then hydrolyzed under vigorous basic conditions to yield 8-fluoro-5-(p-fluorophenyl)-2,3,4,5-tetrahydro-1H-pyrido[4,3-b]indole (an intermediate common to the present processes). The earlier synthesis of flutroline is completed by 2-alkylation with 3-(p-fluorobenzoyl)propyl chloride and reduction of the ketone to an alcohol group with sodium borohydride.

Welch, U.S. Pat. No. 4,014,890, has described an alternative synthesis of the same earlier intermediate 8-fluoro-5-(p-fluorophenyl)-2-carbethoxy-2,3,4,5-tetrahydro-1H-pyrido[4,3-b]indole, viz., condensation of 1,1-di(p-fluorophenyl)hydrazine with N-carbethoxy-4-piperidine.

Massett, U.S. patent application Ser. No. 425,151, filed Sept. 30, 1982 discloses a superior process for the preparation of the earlier and present intermediate 8-fluoro-5-(p-fluorophenyl)-2,3,4,5-tetrahydro-1H-pyrido[4,3-b]indole, alternatively referred to herein as R-H. Massett's process is also specifically disclosed below.

Welch, U.S. patent application Ser. No. 334,195, filed Dec. 24, 1981, describes preparation of flutroline by reductive alkylation of R-H with 2-hydroxy-5-(p-fluorophenyl)tetrahydrofuran. Welch, U.S. patent application Ser. No. 331,494, filed Dec. 17, 1981, describes preparation of flutroline by condensation of R-H with formaldehyde and p-(1-hydroxy-2-propynyl)phenyl fluoride, followed by hydrogenation of the resulting 2-[4-p-fluorophenyl)-4-hydroxy-2-butynyl] intermediate.

The present 2,3,4,5-tetrahydro-1H-pyrido[4,3-b]indoles are alternatively named as 1,2,3,4-tetrahydro-gamma-carbolines. In either case, numbering is as exemplified in the formula for the radical R, which is defined herein as:

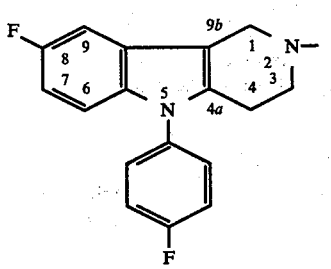

(I)

SUMMARY OF THE INVENTION

The present invention provides a convenient method for preparing flutroline from the intermediate R-H (wherein R is as defined above) and readily available reagents, via a novel, readily purified intermediate. This intermediate is particularly well-suited for the preparation of flutroline in the state of purity required for its use as a therapeutic agent.

The reactions and intermediate involved in the present invention are schematically represented as follows:

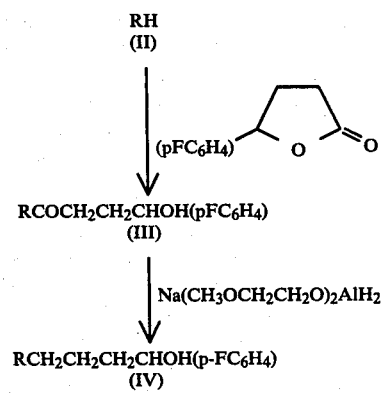

wherein R is as defined above.

A salient feature of the present invention is a process for flutroline (IV) which comprises reduction of 8-fluoro-5-(p-fluorophenyl)-2-[4-(p-fluorophenyl)-4-hydroxybutyryl]-2,3,4,5-tetrahydro-1H-pyrido[4,3-b]indole (III) which sodium bis-(2-methoxyethoxy)aluminum hydride at 80°–110° C. in a reaction inert solvent. It is surprising that this hydride reducing agent will selectively reduce the carbonyl of the primary amide group to methylene, without concomitant, interfering reduction of the 4a,9b-double bond of the group R to 4a,9b-dihydro and/or of the side chain benzylic hydroxyl group to hydrogen.

The above process further comprises the preparation of the compound (III) by the reaction of R-H (II) with 5-(p-fluorophenyl)tetrahydro-2-furanone at 65°–125° C. in a reaction inert solvent.

By the expression "reaction-inert solvent" is intended any solvent which will not react with reactants, reagents, intermediates or products in a manner which adversely affects the yield or quality of the desired product.

5(p-Fluorophenyl)tetrahydro-2-furanone is alternatively named as a 5-substituted dihydro-2(3H)-furanone; as a 4-substituted 4-butanolide; or as a 4-substituted 4-hydroxybutyrolactone.

DETAILED DESCRIPTION OF THE INVENTION

The transformation and intermediates involved in the process of the present invention are schematically represented and summarized above.

For the sodium bis(2-methoxyethoxy)aluminum hydride reduction, aromatic hydrocarbons (such as benzene, toluene, xylenes, chlorobenzene) are well-suited as reaction inert solvents. In fact this hydride is commercially available in such a solvent. The preferred solvent is toluene or a benzene/toluene mixture. The reduction is carried out at elevated temperature (e.g.

80°–110°), conveniently at the temperature of a steam bath. At least 3 equivalents of the hydride (1.5 mole/mole) are required. However, the reaction is not adversely affected by use of an excess of hydride (e.g. 4 equivalents). Indeed, use of some excess is helpful in forcing the reaction to completion in a reasonable period of time. The present selective reduction of amide, while maintaining the 4a,9b-double bond and benzylic hydroxyl is particularly surprising in view of the fact that such an excess of the hydride reducing agent is usually employed.

For the reaction of R-H (II) with 5-(p-fluorophenyl)-tetrahydro-2-furanone, the former is simply warmed with the latter. At least one molar equivalent of the furanone is used, but usually it is more convenient to use an excess in order to force complete conversion of the more valuable R-H in a reasonable time period. Suitable solvents include aromatic hydrocarbons, chlorinated hydrocarbons and ethers as defined above. Again, the preferred solvent is toluene.

8-Fluoro-5-(p-fluorophenyl)-2,3,4,5-tetrahydro-1H-pyrido[4,3-b]indole (R-H, II) required for the above process variations is available by a number of methods (supra), preferably by the method exemplified below.

5-(p-Fluorophenyl)-2-furanone is readily prepared by acid catalyzed lactone formation from 4-(p-fluorophenyl)-4-hydroxybutyric acid. The latter is conveniently prepared by sodium borohydride reduction of 3-(p-fluorobenzoyl)propionic acid, in turn conveniently derived from fluorobenzene and succinic anhydride by the Friedel-Crafts reaction.

The present invention is illustrated by the following Examples. However, it should be understood that the invention is not limited to the specific details of these Examples.

PREPARATION 1

3-(p-Fluorobenzoyl)propionic Acid

A suspension of 170 g anhydrous aluminum chloride and 266 g fluorobenzene was stirred under nitrogen at 10° C. while succinic anhydride (54.4 g) was added in small portions. The mixture was stirred 1.5 hours at 10° to 20° C. and then heated on a steam bath for 45 minutes. The mixture was poured onto 1.2 kg crushed ice containing 280 ml 6N HCl. The product was extracted into methylene chloride, which was washed with water, and then back-extracted into 2N NaOH. The basic extract was treated with activated carbon, and acidified with HCl to precipitate title product, 94 g, mp 98.5°–101° C. Recrystallization from methylene chloride/hexane gave 90.6% recovery, mp 99°–101° C.

PREPARATION 2

5-(p-Fluorophenyl)tetrahydro-2-furanone

To the basic extract of the preceding Preparation was added 0.55 molar equivalent of sodium borohydride portionwise over 45 minutes during which the temperature rose to 41° C. The reaction mixture was allowed to cool to room temperature over 3 hours and then acidified with concentrated HCl. Intermediate 4-(p-fluorophenyl)-4-hydroxybutyric acid was extracted into methylene chloride. One-half volume of 6N hydrochloric acid was added to the organic extract and the mixture stirred at room temperature for 2 hours. The organic layer was separated and vacuum distilled to yield title product as a waxy, low melting solid. Yield: 82%, bp 120°/0.05 mm.

PREPARATION 3

1,1-Di(p-fluorophenyl)urea

Di(p-fluorophenyl)amine (102.5 g, 0.5 mole) and NaOCN (65 g, 1.0 mole) were stirred in 700 ml $CH_2Cl_2$ at 16° C. $F_3CCOOH$ (84.5 ml, 117 g, 1.025 mole) was added as a thin stream over 5 minutes, during which the reaction mixture exothermed to 28° C. The exotherm peaked at 32° C. shortly after addition was complete. The reaction mixture was stirred at 23°–25° for 21 hours, diluted with 350 ml $H_2O$ and stirred 0.5 hour. The organic layer was separated and stirred 0.25 hour with 40 g NaOH in 500 ml $H_2O$. The layers were separated, and the aqueous layer back washed with 100 ml $CH_2Cl_2$. The combined organic layer and back wash was dried ($MgSO_4$), concentrated to 600 ml, diluted with 600 ml isopropanol, reconcentrated to 600 ml, rediluted with 600 ml of fresh isopropanol, reconcentrated to 800 ml, rediluted with 400 ml fresh isopropanol and again reconcentrated to 800 ml. The mixture was cooled to room temperature (product began to crystallize) and then to 0°–5° C. Title product was recovered by filtration, 104.9 g, m.p. 150°–153° C.

PREPARATION 4

Step (a) 1,1-Di(p-fluorophenyl)-3-chlorourea t-Butyl hypochlorite (22.8 g, 0.21 mole) was added to 1,1-di(p-fluorophenyl)urea (49.4 g, 0.2 mole) in 750 ml methanol at 0°–5° and the mixture stirred for 0.5 hour to produce a thin slurry containing step (a) title product.

Step (b) 1,1-Di(p-fluorophenyl)-2-carbomethoxy-hydrazine

At 0°–5° C., sodium methoxide (22.7 g) in 250 ml methanol was added in a thin stream over 5 minutes to the step (a) product mixture. The reaction mixture was warmed to 40°–45° C. for 15 minutes to produce a milky solution of step (b) title product.

Step (c) 1,1-Di(p-fluorophenyl)hydrazine

NaOH (40 g) in 175 ml $H_2O$ was added to the step (b) product mixture. The mixture was distilled at ambient pressure to remove the methanol and the aqueous residue refluxed for 25 hours and cooled to ambient temperature to yield a solution of step (c) title product.

Step (d) 8-Fluoro-5-(p-fluorophenyl)-2-carbobenzoxy-2,3,4,5-tetrahydro-1H-pyrido[4,3-b]indole The solution from step (c) was diluted with 300 ml concentrated HCl, maintaining 35° C. or less. N-Carbobenzoxy-4-piperidone (46.6 g, 0.2 mole) was added and the mixture heated to reflux for 1 hour. The resulting thick slurry was filtered hot with water and methanol wash, 64.6 g. The solids were taken into 400 ml $CHCl_2$, carbon treated, dried ($MgSO_4$), and the $CH_2Cl_2$ displaced with methanol to a final volume of 500 ml and purified step (d) title product recovered by filtration, 60.9 g, identical with title product of Example 2.

PREPARATION 5

8-Fluoro-5-(p-fluorophenyl)-2,3,4,5-tetrahydro-1H-pyrido[4,3-b]indole [RH]

In a Parr bottle were combined 5% Pd/C (10 g of 50% water-wet) and 60 g of 8-fluoro-5-(p-fluorophenyl)-2-carbobenzoxy-2,3,4,5-tetrahydro-1H-pyrido[4,3-b]-indole (60 g, 0.143 mole) in 400 ml ethyl acetate and 100 ml methanol and the mixture hydrogenated at 44–80 psig for 4 hours. Catalyst was recovered by filtration and the filtrate evaporated to solids in vacuo. The residue taken into $CH_2Cl_2$, carbon treated, dried ($Na_2SO_4$) and $CH_2Cl_2$ displaced and hexane by distillation to a final pot temperature of 70° C. The white, crystalline product was recovered by filtration, 35.6 g, m.p. 126°–129° C.

PREPARATION 6

N-Carbobenzoxy-4-piperidone

N-Benzyl-4-piperidone (122.2 g, 0.645 mole) in 500 ml toluene was warmed to 45° C. Benzyl chloroformate (130 ml, 155 g, 0.915 mole) was added in a thin, steady stream, and the reaction mixture heated to reflux for 2 hours, cooled to ambient temperature, diluted with 250 ml $H_2O$ and stirred vigorously 0.5 hour. The organic layer was separated, washed 1×400 ml 6N HCl and then 1×100 ml saturated NaCl, dired ($MgSO_4$), treated with activated carbon, and concentrated to an oil. The oil was distributed between 400 ml ethyl acetate and 400 ml of $H_2O$ containing 67.0 g $NaHSO_3$, stirred 0.5 hour, and the aqueous layer separated, washed with 3 portions of ether, made basic with aqueous NaOH and extracted with fresh ether. The ether layer was dried and reevaporated to yield purified title product as an oil, 136.1 g.

EXAMPLE 1

8-Fluoro-5-(p-fluorophenyl)-2-[4-(p-fluorophenyl)-4-hydroxybutyryl]-2,3,4,5-tetrahydro-1H-pyrido[4,3-b]indole

[R-COCH₂CH₂CHOH(p-FC₆H₄)]

A mixture of 8-fluoro-5-(p-fluorophenyl)-2,3,4,5-tetrahydro-1H-pyrido[4,3-b]indole (0.01 mole) and 5-(p-fluorophenyl)tetrahydro-2-furanone (2.0 g) in toluene was heated on a steam bath overnight. An additional 1.0 g 5-(p-fluorophenyl)tetrahydro-2-furanone was added and the solution was stirred another 5 hours on the steam bath. The reaction mixture was cooled and poured into a stirred mixture of 100 ml water and 100 ml ethyl acetate. Precipitated solids were removed by filtration and the ethyl acetate layer was separated and concentrated in vacuo to an oil. The oil was chromatographed on a short silica gel column, with ethyl acetate as eluant and tlc monitoring. Clean product fractions were combined and evaporated to yield purified title product as an oil, 2.7 g; $R_f$ 0.43 on silica gel tlc with 9:1 $CHCl_3$: methanol as eluant; pnmr/$CDCl_3$/TMS includes delta 4.4 ppm for —OH; ir (KBr) 1626 cm$^{-1}$.

EXAMPLE 2

Flutroline [R-CH₂CH₂CH₂CHOH(p-FC₆H₄)]

A solution of 1.16 g 8-fluoro-5-(p-fluorophenyl)-2-[4-(p-fluorophenyl)-4-hydroxybutyryl]-2,3,4,5-tetrahydro-1H-pyrido[4,3-b]indole (0.0025 mole) in toluene (35 ml) was stirred under nitrogen while 0.0132 mole of sodium bis(2-methoxyethoxy)aluminum hydride (70% in benzene) was added. The resulting mixture was heated on a steam bath one hour, cooled to room temperature and poured into water, and extracted with ethyl acetate. The organic layer was concentrated in vacuo. The resulting residue was chromatographed on silica gel with ethyl acetate as eluant and monitoring by tlc (two solvent systems: 9:1 $CHCl_3$:methanol and acetonitrile) with authentic flutroline as control. Product fractions were combined, evaporated to drynes, the residue triturated with diisopropyl ether to yield title product, 175 mg; m.p. 141.5–144; mixed up with authentic flutroline, no depression.

We claim:

1. 8-Fluoro-5-(p-fluorophenyl)-2-[4-(p-fluorophenyl)-4-hydroxybutyryl]-2,3,4,5-tetrahydro-1H-pyrido[4,3-b]indole.

* * * * *